United States Patent [19]

Dathe et al.

[11] Patent Number: 5,055,126

[45] Date of Patent: Oct. 8, 1991

[54] COMPOSITION FOR INCREASING THE YIELD OF SOYBEANS

[75] Inventors: Wilfried Dathe, Halle/Saale, German Democratic Rep.; Sarah A. Castro Lara, Havanna, Cuba; Reynaldo L. Gutierrez, Havanna, Cuba; Miguel A. Cueto Rodriguez, Havanna, Cuba; Guenther Sembdner, Halle/Saale, German Democratic Rep.

[73] Assignees: Akademie der Wissenschaften der DDR, Berlin, Fed. Rep. of Germany; Akademie der Wissenschaften Kubas, Institut Fuer Grundlagen der Tropischen Landwirtschaft "Alexander von Humboldt", Havanna, Cuba

[21] Appl. No.: 315,171

[22] Filed: Feb. 21, 1989

Related U.S. Application Data

[63] Continuation of Ser. No. 51,956, May 13, 1987, abandoned, which is a continuation-in-part of Ser. No. 543,013, Oct. 11, 1983, abandoned.

[30] Foreign Application Priority Data

Oct. 11, 1982 [CU] Cuba .................................. 35729

[51] Int. Cl.$^5$ .................................. A01N 43/08
[52] U.S. Cl. .................................. 71/89; 71/115
[58] Field of Search .................................. 71/89, 115

[56] References Cited

PUBLICATIONS

Chemical Abstracts 100:3642e.
Datta et al., Chem. Abst., vol. 92 (1980) 124973p.

Primary Examiner—Glennon H. Hollrah
Assistant Examiner—John D. Pak
Attorney, Agent, or Firm—Michael J. Striker

[57] ABSTRACT

With the aim of increasing the yield of soybeans, compositions are disclosed which decrease the high rate of abscission of flowers and young fruit. The composition contains gibberellic acid ($GA_3$) and salicylic acid (SA) in suitable formulations. Application of the composition to the soy plants follows before, during or after the start of blooming. With the aid of the composition according to the invention, the grain yields and length of the shoots can be increased without simultaneously diminishing the stability of the sprouts.

10 Claims, No Drawings

COMPOSITION FOR INCREASING THE YIELD OF SOYBEANS

This application is a continuation application of U.S. Pat. Ser. No. 07/051,956 filed May 13, 1987, now abandoned, which is a continuation-in-part application of U.S. Pat. Ser. No. 06/524,013 filed Oct. 11, 1983, now abandoned.

BACKGROUND OF THE INVENTION

This invention concerns a composition for increasing the yield of soybeans. It has significance for agriculture and serves, particularly, for increasing the grain yield of soybeans. The composition according to the present invention can be used with different types of soybean and different times of sowing.

With grain legumes in general, and, particularly, with soybeans, only 30-40% of the induced flowers develop into ripe fruit. On account of the correspondingly high rate of abscission of flowers and unripe fruit, the grain yield is decreased.

With the aim of obtaining an increased yield with grain legumes, and, particularly, with soybeans, various synthetic and natural growth regulators have been examined (Stutte and Davis 1984, Plant Growth Regulating Chemicals (Edit. L.G.Nickell), Vol. 2, pp. 99–112, CRC Press, Boca Raton, Fla.). To these growth regulators belongs also $GA_3$, which showed yield increasing properties in different soybean cultivars. (Abou-Khadrah et al. 1985, 12th International Conference of Plant Growth Substances, Abstracts p. 12, 25 Heidelberg; Dathe et al. 1986, Biochem. Physiol. Pflanzen 181, 615–621; Stutte and Davis 1984). In some cultivars $GA_3$ caused simultaneously an enhanced shoot growth (cf. Dathe et al. 1986), which results sometimes in a reduction of the shoot stability and may favor the lodging especially in tall cultivars. Thus, the application of $GA_3$ to soybeans was till now limited to small or semi-tall varieties or to tall varieties less sensitive to $GA_3$ in growth stimulation.

In contrast to gibberellic acid, salicylic acid alone is not suitable as an active substance in compositions for increasing the yield of soybeans.

SUMMARY OF THE INVENTION

The invention is therefore directed to developing compositions which, after application, decrease the abscission rate of flowers and young fruit, either by increasing the number of flowers without influence on fruit abscission or by lowering the rate of fruit abscission without negative influence o shoot stability.

According to the present invention compositions are employed for increasing the yield, which contain as active agent gibberellic acid ($GA_3$) and salicylic acid (SA) in addition to customary adjuvants and additives.

The customary adjuvants and additives contained in the compositions according to the present invention are particularly liquid or solid fillers or diluting agents and/or surface-active materials. It is decisive for obtaining the effectiveness that the active substance be combined with suitable dispersing or carrier substances, in order to guarantee an optimal penetration into the plant body.

Moreover, the active substance in the compositions according to the present invention can be used with other active substances in combination, e.g. with growth regulators such as CCC, dimethylmorpholinium chloride (DMC), chloroethylphosphonic acid, herbicides, but also with fertilizer, plant protection and/or soil improvement agents, or formulated together with these.

The composition according to the present invention is prepared by mixing the gibberellic acid and salicylic acid with the additives, and is then provided in the form of solutions, emulsions, suspensions, pastes, powders or granulates. The active substances are used in the form of their formulations or the forms of application prepared therefrom or their mixtures with further components in customary manner, e.g. by means of pouring, splashing, spraying or dusting. The application follows in general at the above-ground parts of the plant. Suitable forms of application are, for example, aqueous solutions, which are stabilized with customary dispersing agents, suspensions, emulsions, spray agents or dusting agents.

With the new compositions for increasing the yield of soybeans, the plants are treated before, during or after the start of blooming. $GA_3$ in concentrations of 0,5–100 ppm (1–50 ml per plant) and in amounts of 1–100 g/ha (1–250μg per plant) and salycylic acid in a ratio from 1:10 to 1:500, preferably in aqueous solution or suspension with or without addition of wetting agents, are applied from one to three times. In general, however, one application is enough.

Through the use of the compositions according to the present invention, the abscission of the flowers and young fruit is significantly decreased, whereby an increased number of fruit per plant and, finally, a higher grain yield is effected, without therewith reducing the height of the plants. The obtained grain yield increase amounts in general from 15 to 35%. The enhanced shoot growth by the composition according to the invention is not accompanied by loss of shoot stability as it can be observed in plants treated with $GA_3$ only. At harvest time the soybean shoot in treated plants is at least as stabil as in control plants and in most treatments even thicker.

The novel features which are considered characteristic for the invention are set forth in particular in the appended claims. The invention itself, however, both as to its construction and its method of operation, together with additional objects and advantages thereof will be best understood from the following description of specific embodiments.

DESCRIPTION OF THE PREFERRED EMBODIMENTS

EXAMPLE 1

Effectiveness of gibberellic acid ($GA_3$) and salicylic acid on the growth and grain yield of soy type G7R-315:

Sowing of the seeds occurred in January in randomized plots, each 1 m², with application of the compositions at the start of blooming. Results are set forth in the following table:

| TREATMENT | APPLICATION AMOUNT (g/m²) | PLANT HEIGHT (cm) | GRAIN YIELD/PLANT (g/plant) | (%) |
|---|---|---|---|---|
| Control | 0 | 53.0 | 4.0 | 100 |
| $GA_3$ | 0.005 | 64.1 | 4.7 | 117.5 |
| Salicylic acid | 0.2 | 51.6 | 4.4 | 110 |
| Salicylic acid | 0.05 | 54.7 | 4.3 | 107 |
| *$GA_3$ + Salicylic acid | 0.005 + 0.1 | 65.3 | 5.3 | 132.5 |
| *$GA_3$ + | 0.005 + 0.05 | 67.2 | 4.7 | 117.5 |

| TREAT-MENT | APPLICATION AMOUNT (g/m²) | PLANT HEIGHT (cm) | GRAIN YIELD/PLANT | |
|---|---|---|---|---|
| | | | (g/plant) | (%) |
| Salicylic acid | | | | |

*At harvest time the soybean shoots of these treatments were more stabile than those ones of the other treatments.

It will be understood that each of the elements described above, or two or more together, may also find a useful application in other types of plant regulation differing from the types of described above.

While the invention has been illustrated and described as embodied in composition for increasing the yield of soybeans, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential features of the generic or specific aspects of this invention.

What is claimed as new and desired to be protected by Letters Patent is set forth in the appended claims.

1. Composition for increasing the yield of soybeans, comprising as active substance gibberellic acid and salicylic acid in an agriculturally acceptable carrier, said gibberellic acid and said salicylic acid in a ratio from 1:10 to 1:20.

2. Composition according to claim 1, further comprising in addition to the active substances liquid or solid fillers or diluting agents.

3. Composition according to claim 2, further comprising surface-active substance with or without further dispersing or carrier substance.

4. Composition according to claim 1, comprising gibberellic acid up to 10%.

5. Method of increasing the yield of soybeans, comprising applying onto or within the locus of said soybeans before, during or after the start of blooming an amount effective to increase the yield of soybeans of the composition according to claim 1.

6. Method according to claim 5, wherein gibberellic acid comprises concentration from 0.5-100 ppm (1-50 ml per plant) with application amounts of 1-100 g/ha (1-250 $\mu$g per plant) in combination with salicylic acid in a ratio from 1:10 to 1:20.

7. Method according to claim 5, wherein application of said composition is made from one to three times.

8. Method according to claim 5, wherein during or after the start of blooming the composition is applied to the above-ground parts of the plants.

9. Process for production of the composition according to claim 1, comprising intermixing gibberellic acid and salicylic acid with the agriculturally acceptable carrier.

10. Process according to claim 9, wherein said composition is formulated as a solution, emulsion, suspension, paste, powder or granulate.

* * * * *